(12) United States Patent
Labowsky et al.

(10) Patent No.: US 7,626,161 B2
(45) Date of Patent: Dec. 1, 2009

(54) ION MOBILITY SEPARATION DEVICES

(76) Inventors: Michael J. Labowsky, 5 Highview Ct., Wayne, NJ (US) 07470; Juan Fernandez de la Mora, 80 Cold Spring St., New Haven, CT (US) 06511

( * ) Notice: Subject to any disclaimer, the term of this patent is extended or adjusted under 35 U.S.C. 154(b) by 341 days.

(21) Appl. No.: 10/556,521

(22) PCT Filed: Feb. 21, 2004

(86) PCT No.: PCT/US2004/005133

§ 371 (c)(1), (2), (4) Date: Apr. 23, 2007

(87) PCT Pub. No.: WO2004/077016

PCT Pub. Date: Sep. 10, 2004

(65) Prior Publication Data

US 2007/0272847 A1    Nov. 29, 2007

Related U.S. Application Data

(60) Provisional application No. 60/449,080, filed on Feb. 22, 2003.

(51) Int. Cl.
*B01D 59/44* (2006.01)
*H01J 49/00* (2006.01)

(52) U.S. Cl. .................. 250/283; 250/281; 250/282; 250/287; 250/288; 250/290; 250/294

(58) Field of Classification Search ......... 250/281–283, 250/287, 288, 290, 294
See application file for complete search history.

(56) References Cited

U.S. PATENT DOCUMENTS 5,218,203 A    6/1993    Eisele et al.

(Continued)

FOREIGN PATENT DOCUMENTS

WO    WO 03/041114 A2    5/2003

OTHER PUBLICATIONS

J. F. De La Mora: "Diffusion Broadening in Converging Differential Mobility Analyzers", Journal of Aerosol Science, vol. 33, 2002, pp. 411-437, XP002444088, Pergamon; Abstract; Figure 4.

(Continued)

*Primary Examiner*—David A Vanore
*Assistant Examiner*—Meenakshi S Sahu
(74) *Attorney, Agent, or Firm*—Hoffmann & Baron, LLP

(57) ABSTRACT

The invention describes a system and method to separate ions (and charged particles) suspended in gas based on their ion electrical mobility. Most common ion mobility analyzers involve two parallel plate (or concentric cylinder) elements (electrodes) between which is imposed an electrical field perpendicular to a sheath gas flow field between the cylinders. Separation occurs because high mobility ions tend to follow the electrical field while low mobility ions tend to follow the flow field. This invention describes various configurations of electrical elements and sheath gas flow fields for ion mobility separation devices with unique performance characteristics. These characteristics include devices in which: the ion inlet and outlet are on the same element; the inlet and outlet are at the same voltage; the outlet is upstream from the inlet; the outlet is on the axis; the inlet is on the axis; and the ions are focused on the outlet.

39 Claims, 7 Drawing Sheets

U.S. PATENT DOCUMENTS

| | | | |
|---|---|---|---|
| 5,606,112 | A | 2/1997 | Flagan et al. |
| 5,869,831 | A * | 2/1999 | De La Mora et al. ........ 250/288 |
| 5,936,242 | A * | 8/1999 | De La Mora et al. ........ 250/288 |
| 6,124,592 | A * | 9/2000 | Spangler .................... 250/287 |
| 6,320,572 | B1 | 11/2001 | Takabayashi et al. |
| 7,161,143 | B2 * | 1/2007 | De La Mora et al. ........ 250/287 |

OTHER PUBLICATIONS

W. Winklmayr et al.: "A New Electromobility Spectrometer for the Measurement of Aerosol Size Distributions in the Size Range From 1 to 1000 nm", Journal of Aerosol Science, vol. 22, No. 3, 1991, pp. 289-296, XP002444089 Pergamon, Abstract; Figures 1, 2.

R. Strydom et al.: "A Mobility Spectrometer for Measurement of Initial Properties of 218 Po", Journal of Aerosol Science, vol. 21, No. 7, 1990, pp. 859-873, XP002444090, Pergamon, Abstract; Figures 2, 3.

* cited by examiner

ION MOBILITY SEPARATION DEVICES

CROSS-REFERENCE TO RELATED APPLICATIONS

This application claims the benefit of U.S. Provisional Patent Application No. 60/449,080 filed Feb. 22, 2003 which is incorporated by reference herein in its entirety.

STATEMENT REGARDING FEDERALLY SPONSORED RESEARCH OR DEVELOPMENT

Not relevant.

REFERENCES TO SEQUENCE LISTING, TABLES OR COMPUTER PROGRAM LISTING APPENDIX ON COMPACT DISK

None.

BACKGROUND OF THE INVENTION

1. Field of the Invention

This invention generally relates to a method and apparatus for sizing and classifying ions suspended in gas based on their ion mobility.

2. Description of the Related Art

The separation and/or sizing of ions according to their different mobilities is widely used for a variety of applications. There term "ion" is used here to include not only molecular ions but also charged particles. Devices that separate ions by their ion mobilities (Z) will be referred to here as "Mobility Analyzers" (MA), even though their use may be more general. Separation of ions in time (SIT) can be achieved in pulsed systems by use of just electric fields. This is the most commonly used technique for ion separation in a gas. Separation in space (SIS) is typically achieved by combining electric and fluid flow fields. SIS mobility analyzers have the advantage of being able to yield monomobile ion fractions which are steady rather than pulsed, and are, therefore, best suited for further use downstream in other instruments. SIS mobility analyzers have been most successful in aerosol separation in the ranges between 10 and a few hundred nm, but is now suitable also to cover the 1-10 nm range at resolutions as high as those typical of the best SIT instruments for ion analysis.

This invention describes some novel designs for SIS type mobility analyzers. Common to all SIS instruments, a small flow of ions is introduced through a narrow slit or small orifice (the "Inlet") into a much larger laminar flow of sheath gas within a region where the ions move under the simultaneous action of the sheath gas velocity field ($U(x)$) and the electric field ($E(x)$), where x is the vector determining position. The sheath gas flow should be substantially ion free. The flow and electric fields are arranged so as to separate the ions by their mobilities (Z). The ion mobility is related to the diffusivity (D)) of the ion by equation 1:

$$Z_i = DNe/(kT) \qquad \text{Equation 1.}$$

where e is the elementary charge, N is the total number of charges on the ion, K is the Boltzman constant and T is the absolute temperature.

The region in which the separation occurs is referred to as the "Analyzing Region." The path followed by the ions in this analyzing region is a direct function of the ion's mobility. The term "trajectory" is used here to mean the average path followed by ions with the same Z. Individual Z-ions may deviate from this average path due to diffusion or space charge effects, but the average of all the paths followed by the Z-ions would be the trajectory of the k-ions. The trajectories of very low mobility ions tend to follow the sheath gas flow field ("flow field") while the trajectories of very high mobility ions tend to follow the electric field. The trajectories of moderate mobility ions are in between these two extremes. After separation, a small fraction of the separated ions pass into an "Outlet." This outlet may be either a second slit or orifice through which the ions are extracted or a well defined region in which the ion charge is collected. While small flow of gas usually accompanies the ions as they are injected into and/or extracted from the analyzing region, ions may be introduced into or extracted by purely electric means, without a net flow of gas, as for example in the inlets of Strydom R., Leuschner A. H., Stoker P. H. (A Mobility Spectrometer for Measurement of Initial Properties of Po-218, Journal of Aerosol Science, 21 (7): 859-873 1990). Whether an ion is physically extracted from the outlet or extracted bt electrical means, the ion is said to be collected at the outlet. MA devices are usually of one of two types: differential or cumulative. Differential mobility analyzers (DMA) are designed so that ions of different mobilities strike the boundary of the analyzing region at points which are dependent on the ion mobility. An outlet is positioned so that ions within a narrow range of the desired mobility are collected. Cumulative mobility analyzers (CMA) are designed so all or a relatively wide range of ion mobilities above or below a certain critical value reach the outlet.

One goal of MA devices is to spatially separate ions of similar mobilities by the greatest possible distance. The ions move along their trajectories in the analyzing region with a certain velocity. The velocity of an ion is a function of the local values of $U(x)$ and $E(x)$. FIG. 1 is a schematic drawing of a common prior art MA. This MA consists of only two parallel conducting plates: a top plate (110) and a bottom plate (120). These plates will be referred to as elements. The prior art device, therefore, has only two elements: the top element (110) and the bottom element (120). The term "element" can be used interchangeably with the term "electrode."

A voltage difference ($V_c$) is placed on the top plate with respect to the bottom plate so that the $E(x)$ field is perpendicular to the plates and acts to push the ions from the top plate to the bottom plate. Sheath gas (150) passes from right to left between the plates so the $U(x)$ field acts to push the ions parallel to the plates from right to left. Hence in this prior art MA, $E(x)$ and $U(x)$ are perpendicular at all points.

In order to analyze the performance of MA devices, it is convenient to work in terms of the dimensionless quantities as expressed in equation 2 a-f:

$$u_i = U_i/U_c \qquad \text{Equation 2a}$$

$$u_g = U_g/U_c \qquad \text{2b}$$

$$E^* = E/(V_c/L) \qquad \text{2c}$$

$$V^* = V/V_c \qquad \text{2d}$$

$$K = ZV_c/(U_cL) \qquad \text{2e}$$

$$x^* = x/L \qquad \text{2f}$$

where $U_c$ is a characteristic sheath gas velocity, and L and $V_c$ are the characteristic length and voltage difference, respectively. A convenient value of $U_c$ is the average sheath gas velocity into the analyzing region. The dimensionless ion velocity may be written as equation 3:

$$u_i(x^*) = u_R(x^*) + KE^*(x^*) \quad \text{Equation 3.}$$

For calculation purposes, if it further assumed that the sheath gas flow is idea, in the sense that both the $u_g(x^*)$ and $E^*(x^*)$ vector fields given by the gradient of a scalar potential governed by the Laplace equation. So, in order to explore various MA designs one needs an efficient way of solving the Laplace Equation. A singularity method was used in this work. In this method, N singularities (line singularities for 2D; ring and/or point singularities for axi-symmetrical) are positioned outside of; but close to the analyzing region. N equations for the N unknown singularity source strengths are provided by specifying the boundary conditions at N points on the boundary of the analyzing region. The N simultaneous linear equations are then solved for the N unknown singularity strengths. Two calculations are required, one each for $E^*$ and $u_g$. The Laplace equation must be solved subject to a set of boundary conditions for a given device. In the case of $E^*$, the voltage is usually specified for the various elements. The boundary conditions for flow field require that a there is a certain flow rate into the analyzing region and the walls of the analyzing region are impenetrable to the gas except at inlets and outlets where there may be a net flux of gas. Knowing these singularity strengths, the field ($E^*(x^*)$ or $u_g(x^*)$) at any point inside the analyzing region can be found by superimposing the fields of the N singularities. While a singularity method was used in the work that follows there are many ways of solving the Laplace Equation known to those skilled in the art. The particular method of solution is not germane to the invention. Suffice it to say that by solving the Laplace Equation in dimensionless form using the above dimensionless quantities, the trajectories of ions with various mobilities can be traced through the analyzing region starting at the inlet in explicit terms of K instead of Z. The trajectories are calculated by repetitive use of Equation 3 as follows. The velocity at the inlet of an ion with a given K is first calculated by evaluating the $E^*$ and $u_g$ at the inlet point and applying Equation 3. The ions are then allowed to move to a new point a small distance in the direction of the inlet ion velocity. $E^*$ and $u_g$ are then calculated at this new point and a new $u_i$ is found from Equation 3. The ion then moves a short distance based on the new $u_i$ and the process is repeated until the ion strikes a wall, an outlet or passes out of the analyzing region. Knowing the inlet width and flow rate, and the outlet width and flow rate the range of K ($\Delta K$) for ions that can be collected at the outlet can be determined for any configuration of a device.

The ion trajectories (160) are shown as solid lines emanating from the inlet (130) for the prior art DMA in terms of K in FIG. 1. An ion mobility spectrum is produced by measuring the signal (current) of ions reaching the outlet (140) as a function of the voltage difference ($V_c$) between the plates. In dimensionless terms, such a mobility spectrum can be cast in terms of a "Transmission" as a function of K. The transmission is caressed in terms of the percentage of ions of a certain K input into the MA which can reach the outlet and is independent of rate of input of these ions at the inlet. The signal in the ion mobility spectrum would then be proportional to the rate of input of K-ions multiplied by the transmission of that K-ion. The reason for using dimensionless quantities in this analysis is that while $E(x)$ varies with $V_c$, $E^*$ is a function only of the device geometry. The dimensionless voltage ($V^*$) has a value of 1 on the top plate (110) and 0 on the bottom plate (120). After calculating the ion trajectories in terms of K, we find that ions within a small range of a certain K, called $K_o$, can reach the outlet. The corresponding values of ion mobilities that can reach the outlet ($Z_o$) are found by inverting Eqn. 2d to become equation 4:

$$Z_o = K_o U_c L/V_c \quad \text{Equation 4.}$$

Hence, once $K_o$ is determined, the ion mobilities that reach the outlet can be calculated for a given voltage difference between the plates ($V_c$).

In FIG. 1, the ions follow trajectories (160) from the inlet (130) on the top plate (110) to the bottom plate (120). The slope of the trajectory line decreases with decreasing ion mobility. Hence, high mobility ions strike the bottom plate upstream from the lower mobility ions. The outlet (140), located on the bottom plate (120), is positioned to collect ions of the desired mobility.

A mobility spectrum may contain one or more peaks, corresponding to each of the ion species present in the inlet sample. The performance of a device is expressed in terms of Resolution (Res) per equation 5:

$$\text{Res} = Z_{mean}/\Delta Z \quad \text{Equation 5.}$$

where $Z_{mean}$ is the mobility corresponding to the center of a given peak. For DMA's, $\Delta Z$ is the width of the peak at half the height of the peak. For CMA's $\Delta Z$ is the Z-difference between no signal and full signal. Alternatively, the resolution can be expressed in terms of K instead of Z:

$$\text{Res} = K_{mean}/\Delta K \quad \text{Equation 6.}$$

Where $K_{mean}$ is the value of K at the center of a peak. For DMA's, $\Delta K$ is the width of the transmission peak at half-height. For CMA's, $\Delta K$ is the K-difference between no transmission and full transmission. The resolution may also be expressed as the inverse of the definitions given above. This inverse resolution (IRes) is expressed as in equation 7:

$$\text{IRes} = 100/\text{Res} \quad \text{Equation 7.}$$

The larger the value of Res, the smaller is the value of IRes. So a high resolution would mean a small IRes. It is desirable to have the resolution as high as possible. In other words, it is desirable to have the width at half height of a peak ($\Delta Z$, $\Delta K$) to be as small as possible. If the resolution is low, it is possible that when two ions with similar mobilities are present, their ion mobility spectrum peaks may be so close that they merge into a single peak and their individual identities would not be detected. A high resolution device, on the other hand, would be able to show, or resolve, the two peaks, making identification of the individual ion species easier. The resolution of a device is affected by several factors including the widths and flows of the inlet and outlet, ion spread in the analyzing region resulting from diffusion and sheath gas irregularities such as turbulence and boundary layer effects. As was shown in Rosell-Llompart et al., Minimization of the diffusive broadening of ultrafine particles in differential mobility analyzers, in Synthesis and Characterization of Ultrafine Particles, pp. 109-114 (1993), it is desirable to have the sheath gas flow rate as high as possible in order to minimize diffusion spreading and boundary layer effects. The rate of sheath gas flow is usually characterized by the Reynolds Number (Re)

$$Re = 2L \, Ug,\text{ave}/\nu \quad \text{Equation 8}$$

Where $\nu$ is the kinematic viscosity of the gas and Ug,ave is the average gas velocity in a channel. A high sheath gas flow rate means the Reynolds number should be as high as possible to minimize diffusive effects. There are, however, limitations on the maximum sheath gas flow rate before the onset of turbulence. Achieving high Reynolds number flow without turbulence is difficult. de Juan and de la Mora (J. Aerosol Sci. 29, 617-626, 1998) showed how to achieve Reynolds numbers as high as 5000 in a device similar to that disclosed by Winklmair, et.al., A New Electro-mobility Spectrometer for the Measurement of Aerosol Size Distributions in the Size Range from 1 to 1,000 Nanometers, J. Aerosol Sci., Vol. 22, pp 289-296 (1991). Some aspects of achieving high Reynolds numbers while avoiding turbulence were disclosed by de la Mora, et.al in U.S. Pat. Nos. 5,869,831 and 5,936,242 by reducing perturbations in the inlet sheath gas flow by using stages of laminarizing screens and filters followed by rapid acceleration of the sheath gas prior to introduction into the analyzing region. Using this technique Reynolds numbers of the order of 35,000 were attained before the onset of turbulence.

The MA shown in FIG. 1 may be described as two dimensional (2D) because the analyzing region is between two parallel plates. An alternative to this 2D design is one in which the top and bottom plates are replaced by concentric cylinders. This alternative design is called "axi-symmetric" (AS) because it is symmetrical about the cylinder center line (axi). The trajectories of the ions in the AS design are schematically the same as in the 2D design. It should be noted that in the prior art MA devices all ions within the analyzing region move continuously from the top plate to the bottom plate. This means that the velocities of the ions, as they move along their trajectories, are at all points in the analyzing region greater than zero.

A few previous authors have investigated non-traditional MA configurations with the goal of achieving certain desirable operational advantages. Loscertales, Drift Differential Mobility Analyzer, J Aerosol Sci., Vol. 29, pp1117-1139, 1998 described a DMA device in which an electric field antiparallel to the fluid flow is imposed in addition to the traditional transverse field. The main novelty of the Loscertales device stems from the fact that it substitutes the traditional two-element DMA geometry by one with effectively an infinite number of infinitesimal elements. In the particular case where the electric and fluid flow fields are both spatially uniform Loscertales demonstrates the possibility of singularly high resolving powers. His design uses two surfaces supporting constant tangential electric fields rather than constant voltages. A working device based on the Loscertales principles, however, has yet to be built. Tammet, The Limits of Air Ion Mobility Resolution, Proc. 11$^{th}$ Int. Conf. Atmos. Electr., NASA, MSFC, Alabama, 626-629, 1999, described a working device called an Inclined Grid Mobility Analyzer (IGMA) in an attempt to simulate the fields in a Loscertales DMA. In the IGMA, the sheath gas passes through two inclined electrified screens that are held at different voltages. The voltage on the screens generates the electrical field for the analyzing region located between the screens. The interference of the sheath gas flow as it passes through the screens, however, produces a complicated aerodynamic flow (turbulence) which is one of the shortcomings of the device. The screens in the Tammet device are what may be called perturbing screens. A perturbing screen is one in which introduces turbulence in the analyzing region. A non-perturbing screen is one which is downstream of the analyzing region or is in a position upstream of the analyzing region where the sheath gas flow channel has a wider area and substantially smaller Reynolds Number, so turbulence is not generated or if turbulence is generated it decays substantially downstream of the screen and has little if any affect in the analyzing region. The Tammet device has a large voltage jump at the inlet resulting in significant losses of ions before they can enter the analyzing region. To moderate these losses, Tammet uses an inlet opening that is much wider than is typical for the traditional MA devices such as that shown in FIG. 1. Indeed, if the inlet in the Tammet device were narrow, that is similar in width to those in traditional MA devices, few if any ions would be able to enter the analyzing region. With a few other relevant exceptions (Flagan, R. C. and Zhang, S. H., 1997, Radial differential mobility analyzer, U.S. Pat. No. 5,596,136; J. Fernandez de la Mora, Diffusion broadening in converging differential mobility analyzers, J. Aerosol Science, 33, 411-437, 2002), traditional DMA analyzing region designs have tended to be limited first geometrically, to parallel or coaxial cylindrical geometries. Second, except for Loscertale's Drift DMA, which is still only conceptual, almost all DMA designs involve two elements only. Third, the ion inlet and outlet have always been located in different elements. From these later two restrictions alone two serious complicating features follow inevitably. If a voltage difference between the elements is necessary to establish a field in the analyzing region, while the inlet is in one electrode and the outlet is located on the other, the inlet and outlet lines need to be at different voltages. This then precludes caving the analyzing region of the DMA from a single piece of metal, which would be ideal for achieving a precise alignment. A second related problem is that the sampled aerosol is often at or near ground (such as in atmospheric sampling, or when sampling from aerosol generators that cannot be floated), while the aerosol detector often also needs to be at or near ground. Consequently, a high voltage jump needs to be imposed either on the inlet of the outlet, and the associated fields lead to considerable sample losses, especially in the nanometer size range. This problem is particularly acute in cases involving the use of two or more MAs in tandem, since the losses associated to each voltage jump grow exponentially with the number of MA stages. In light of this, it would be desirable to have MA devices in which the voltage difference between the inlet and outlet is as small as possible.

BRIEF SUMMARY OF THE INVENTION

The present invention comprises a method and apparatus for separating ions suspended in gas in a mobility analyzer having an inlet and an outlet said method comprising the following steps:
  a) introducing a stream of ions of into an analyzing region through said inlet;
  b) introducing laminar sheath gas flow into said mobility analyzer upstream from said analyzing region;
  c) maintaining of said laminar sheath gas flow as substantially laminar in the said analyzing region;
  d) providing an electrical field in said analyzing region wherein said electrical field is generated by elements charged to various voltages said elements being separated by junctions;
  e) using the said laminar sheath gas flow and the said electrical field to separate the ions by mobility in the said analyzing region;
  f) collecting said separated ions within in said outlet.

The said elements separated by junctions have unique separation characteristics. For example, Devices which use said elements may have some or most of the following features: focusing of the separated ions on the outlet; said inlet and the said outlet to be on the same element, or on different elements that are at the same, or nearly the same voltage; said outlet to be on the centerline/axis of a device; said inlet to be on the centerline/axis of a device; said outlet to be upstream of said inlet.

The invention also shows that the affects of said elements may be augmented and/or simulated by the use of auxiliary flows of sheath gas.

BRIEF DESCRIPTION OF THE DRAWINGS

The figures below depict various aspects and features of the present invention in accordance with the teachings herein.

DETAILED DESCRIPTION OF THE INVENTION

Three Element Devices

Figure 1:
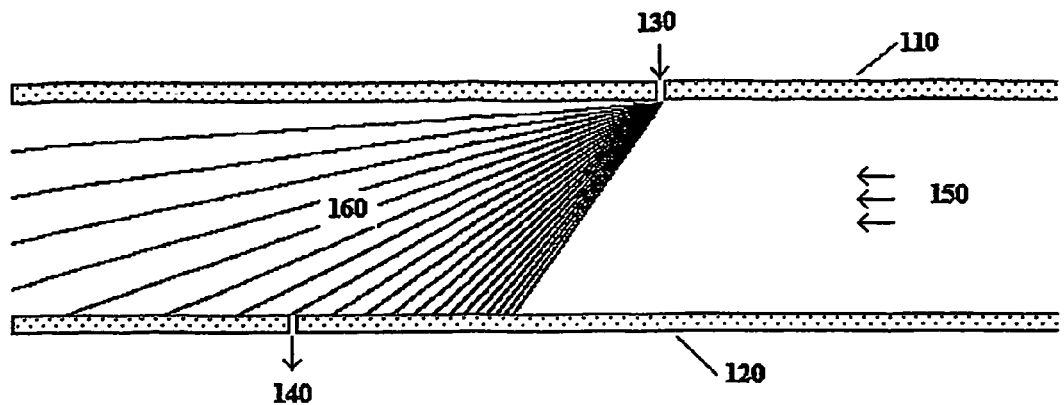
FIG. 1 is a schematic cross-sectional view of a common prior art device including ion trajectories.

The present invention has many possible embodiments. The purpose of the following sections is to show a few of these embodiments which demonstrate how specially configured elements can be used to obtained the desired characteristics. Others embodiments should be obvious to those skilled in the art. FIG. 2 shows one embodiment of the current invention. The device shown is similar to the one shown in FIG. 1. It has a top plate (200) and a parallel bottom plate. In contrast to FIG. 1, the bottom "plate" has two elements (210,220). There is a voltage difference between the bottom left (220) and bottom right elements (210). A "junction" (250) separates the bottom left (220) and bottom right (210) elements and enables these elements to be at different voltages. To be considered a junction, the junction must be sufficiently near the analyzing region so the strong electrical fields near the junction affect the trajectories of the ions in the analyzing region. Physically, a junction may be, for instance, a thin strip of insulating material or gap of sufficient resistance to prevent arcing between the elements. A construction that generates large voltage jumps near the inlet or outlet with the resulting loss of Zo-ions would not be considered a junction.

The device shown in FIG. 2, therefore has a total of three elements: the top plate (200) and the left (220) and right (210) sections of the bottom plate and one junction (250). The characteristic length is L, the distance between the top and bottom plates and the characteristic voltage is the potential difference between the bottom electrodes. This means if the top element is at ground, then the left bottom element (220) is at a dimensionless voltage ($V_{bl}^*$) of +0.5 and for the bottom right element (210) $V_{br}^*$=−0.5. The ion inlet (230) is on the top plate (200) upstream from the junction (250) in the bottom plate. The potential difference between the bottom elements is such that an ion in the E(x)) field created by this potential difference acts to push the ions near the junction in a direction opposite to the sheath fluid flow. The percent ion inlet flow ($Q_i$) is equal to the ion outlet flow percent ($Q_o$) and the inlet (230) and outlet (240) are symmetrical above the junction. In this figure the distance between the inlet (230) and outlet (240) is L. Laminar sheath gas flows (260) into the analyzing region from right to left. Since the analysis is presented dimensionless terms, reference is made to K instead of Z.

The solid lines (280,290) in FIG. 2 are the trajectories of ions for various K (mobilities). The broken curve indicates a particular trajectory called the ion stagnation trajectory. An ion stagnation trajectory is one that passes through an ion stagnation point (270). Ions that follow this trajectory have a K designated as $K_s$. An ion stagnation point is created where the product of K and the local dimensionless field strength is equal and opposite to the local flow field (K $E^*(x^*)=-u_g(x^*)$) and the $K_s$-ion velocity goes to zero. The ion stagnation trajectory starts at the inlet (230) and goes to the ion stagnation point (270) where it splits into two branches: one branch (275A) leading to the outlet (240), the other branch (275B) leading to the bottom right element (210). The ion stagnation trajectory has the unique property of separating ions with $K>K_s$ from ions with $K<K_s$. It is this separation of high and low mobility (K) ions that makes the ion stagnation trajectory and ion stagnation point important. FIG. 2 clearly shows two sets of ion trajectories separated by the stagnation trajectory. One set (290) is for ions in which $K>K_s$. These ions do not reach the indicated outlet (240) but strike the bottom right element (210). The other set (280) is for ions with $K<K_s$. The ions in this set (280) leave the inlet (230), traverse the analyzing region and are focused on the indicated outlet (240). The fact that all ions with $K<K_s$ are focused on the outlet means that this device acts like a low-pass filter, or a CMA.

The focusing effect observed may be understood by noting that ion trajectories are characterized by a constant value of the group $\eta(x)=\Psi(x)+K\Lambda(x)$, where $\Psi(x)$ and $\Lambda(x)$ are the usual stream functions for the flow and electric fields, respectively. The ions that are reflected return to the original plate from which they are emitted, where $\Psi(x)$ takes the same value as at injection. This coincidence holds independently of the ion mobility. For an ion of any mobility to be able to return to that plate $\Lambda(x)$ must take the same value at the arrival point as at the injection point. But if both stream functions take the same value at the injection and the focusing point, then, the group $\eta$ is conserved for all ions independently of their mobility. In other words, if one ion returns to the plate where it was emitted, many other ions of different mobilities originating in the same point can also return to exactly the same final point, hence the focusing observed. This reasoning shows that ions of widely differing K can be focus into one point, but it does not show that all ions can be focused. Indeed, ions with $K>K_s$ cannot penetrate the junction plane because the values of $\Psi$ and $\Lambda$ on this plane ($\Psi j(y)$, $\Lambda j(y)$) are such that for any point a distance y above the junction, $\Psi j(y)+K\Lambda j(y)<>\Psi_{in}+K\Lambda_{in}$, where "in" indicates conditions at the inlet. Hence, the ion cannot cross the junction plane.

Figure 3:
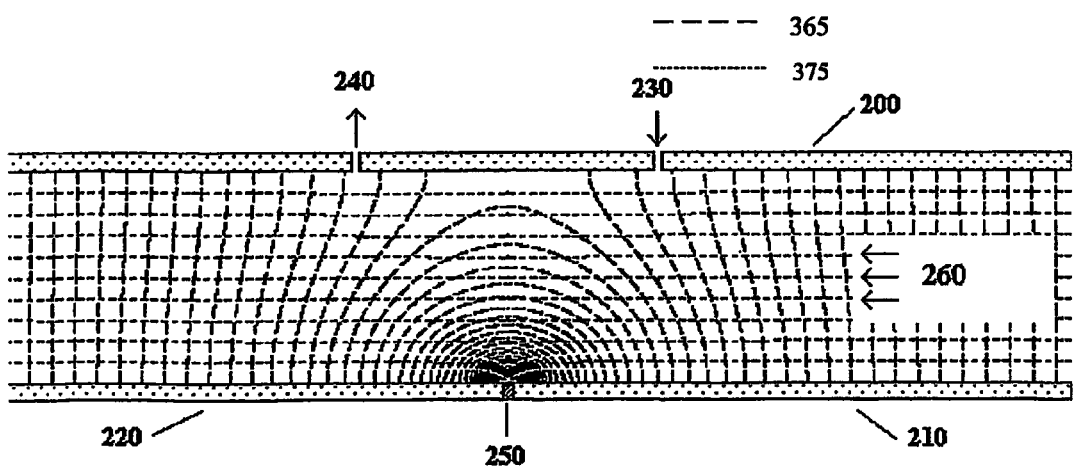
FIG. 3 shows the electrical fieldlines and flow field in a three element device.

FIG. 3 shows the dimensionless electric field as dashed lines (365) and the sheath gas stream as dotted lines (375) that exist in the device. The streamlines are parallel to the plates and point in the direction of the indicated sheath gas flow (260) while the field lines strike the top and bottom plates at 90 degree angles. The shapes of the fieldlines (365) are symmetrical about the junction plane. To the right of the junction (250), however, the fieldlines (365) tend to point from the top plate (200) to the bottom right element (210) while to the left of the junction (250), the field points from the bottom left (220) to the top element (200). In the region between the inlet and the outlet, the electric field lines (365) and the streamlines (375) cross at varying angles. In the vicinity of the inlet, the electric field is nearly perpendicular to the streamlines, pulling the ions into the flow and away from the inlet. In the center of the analyzing region near the junction (250), the electric field is anti-parallel to the streamlines. Near the indicated outlet, the electric field (365) is again nearly perpendicular to the streamlines (375), but acts toward the top plate and, thus, pulls the ions towards the outlet (240). The changing of the electric field with position indicates that the direction of the electric field varies within the analyzing region and is not always perpendicular to the flow field.

Figure 4:
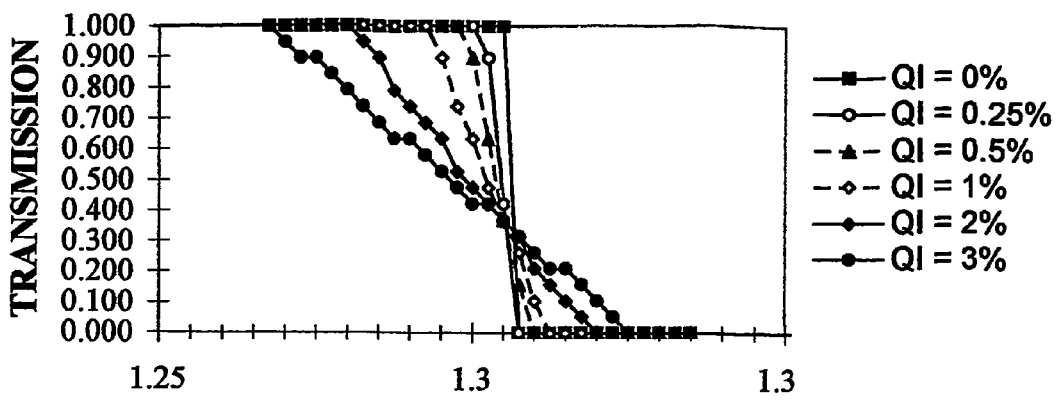
FIG. 4 shows the transmission as a function of K for various inlet ion flow fractions for a three element device

FIG. 4 shows the Transmission curves for the above three element device for various $Q_i$. Qi is the flow rate through the inlet as a percentage of the total sheath gas flow rate. As can be seen from this figure, for small values of $Q_i$, the transition from no transmission to full transmission is abrupt and occurs over a small increment of K, indicating good resolution. For example, the resolution, as defined in Eqn.(3), for $Q_i$=0.25% is 260. As $Q_i$ increases, the transition occurs over a wider increment of K and the resolution, therefore, decreases. The resolution is 75 for Qi =1% and 35 for Qi =2%. The decrease in resolution with increasing inlet flow is a reflection of the increased ion spread at the inlet due to the increased inlet flow.

Figure 2:
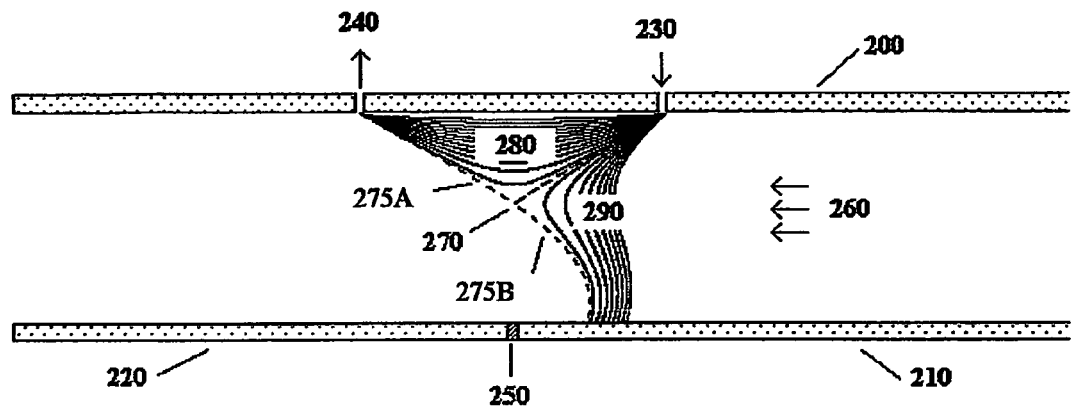
FIG. 2 shows as a schematic cross-sectional view of a three element device including ion trajectories.

The device shown in FIG. 2, therefore, has at least five features not found in the traditional DMA of FIG. 1: 1) the presence of an ion stagnation point 2) The outlet is on the same element as the inlet. 3) the ions are focused on the outlet. 4) the electric field and the sheath gas flow vectors cross are varying angles within the analyzing region 5) the outlet is at the same potential as the inlet. A device in which the inlet and outlet are at the same voltage (electrical potential) and where the ion trajectories going from the inlet to the outlet do not travel through the vicinity of a junction will be referred to as an isopotential device. Isopotential devices represent an important class of MA's for several reasons. First, their use is not limited by prior patents, which have typically required a voltage difference between inlets and outlets. Second they avoid outlet losses associated with voltage jumps, which makes them ideally suited for use of one or several MA devices in tandem with other MAs or even with other instruments such as a mass spectrometer for further analysis of the effluent. While the device shown in FIG. 2 was 2D an analogous axi-symmetrical (AS) device can also be fashioned by replacing the parallel plates with concentric cylinders. It should also be mentioned that the strike points of high mobility ions (290) on the bottom right element (210) are dependent on the ion mobility. The higher the mobility, the further upstream the strike point. A DMA outlet could be placed in the bottom right element (210).

This particular embodiment of the invention shows how the presence of one junction affects the characteristics of an MA. In this case the bottom right element (210) is attractive with respect to the bottom left element (220). If the polarity of these elements were reversed, so that the right element was repulsive with respect to the left element, a different MA would be achieved. The ions in this reversed polarity device would strike at points on the bottom left element (220) according to their ion mobility with the higher mobility ions striking closer to the junction (250) than lower mobility ions. A DMA outlet could then be placed on the bottom left (220) element, but this outlet would not be isopotential.

Six Element Devices

By specially configuring several elements, separated by junctions, MA devices with unique characteristics can be achieved. FIG. 5 shows a schematic cross-sectional view of a device with six elements along with various ion trajectories. The device consists of two parallel plates separated by a distance L, the characteristic distance. The sheath gas (560) flows as indicated between the plates from right to left. The bottom plate has a bottom left element (525) and a bottom right element (520) separated by a junction (541). The characteristic voltage for this device is the potential difference between the bottom left ($V_{bl}$) and right ($V_{br}$) voltages. Hence in dimensionless terms, $V_{bl}$*=0.5, $V_{br}$*=−0.5. The top plate has four elements separated by three junctions (540). The top elements are arranged symmetrically above the bottom junction (541). The inlet (530) and outlet (535) are located on the top right (500) and top left (515) elements, respectively. The top left ($V_{tl}$) and top right ($V_{tr}$) potentials are set at ground. The top middle right element (505) is at an attractive voltage of $V_{mr}$, while the top middle left element (510) is at repulsive voltage ($V_{ml}$) such that $V_{mr}$=−$V_{ml}$. In this particular device, the top middle elements (505, 510) are of half unit length (L/2) and the inlet (530) is a unit distant (L) upstream from the bottom junction and the outlet is a unit distance (L) downstream from the bottom junction. As will be shown, this device acts like an ion mobility filter in a sense because it allows only ions within a certain mobility range to reach the outlet. This mobility range may be considered to be the bandwidth of the ion mobility filter.

Figure 5A:
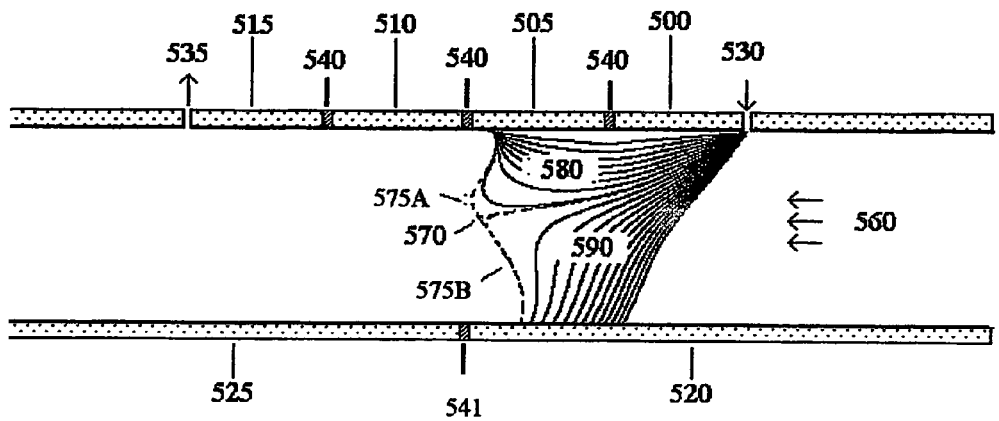
FIG. 5A-D show schematic cross-sectional views of a six element device including ion trajectories.
Figure 5B:
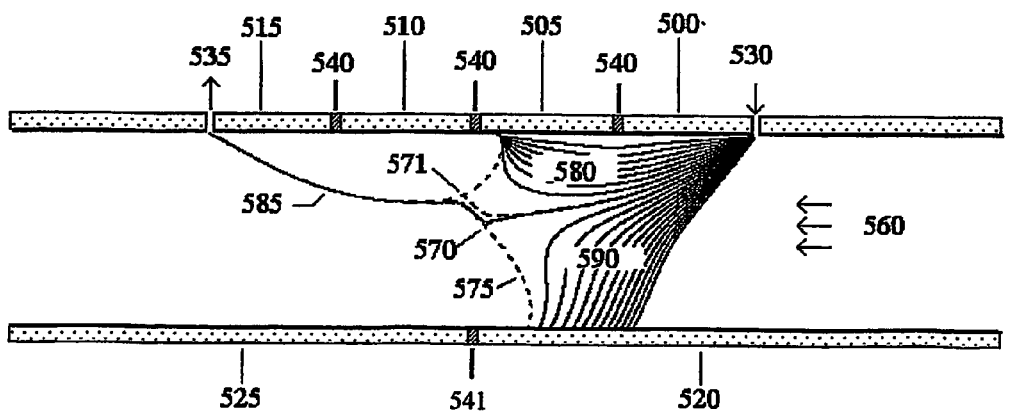
Figure 5C:
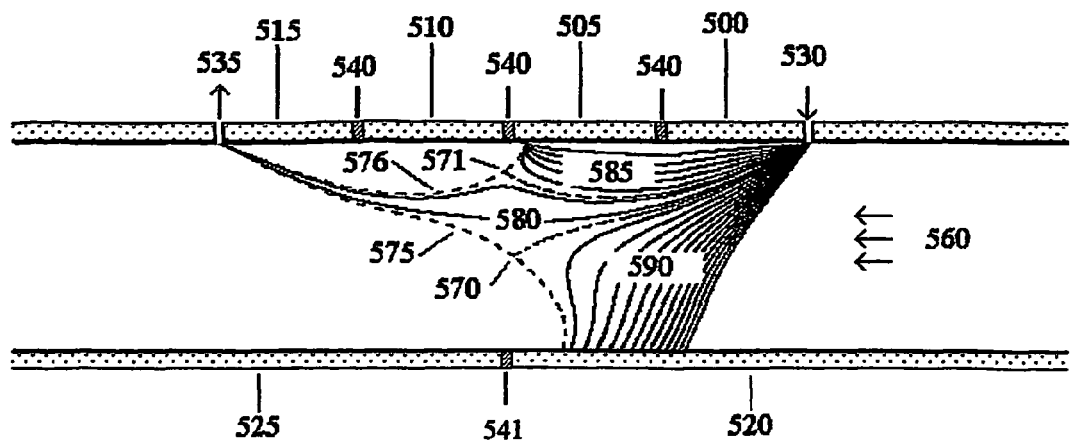
Figure 5D:
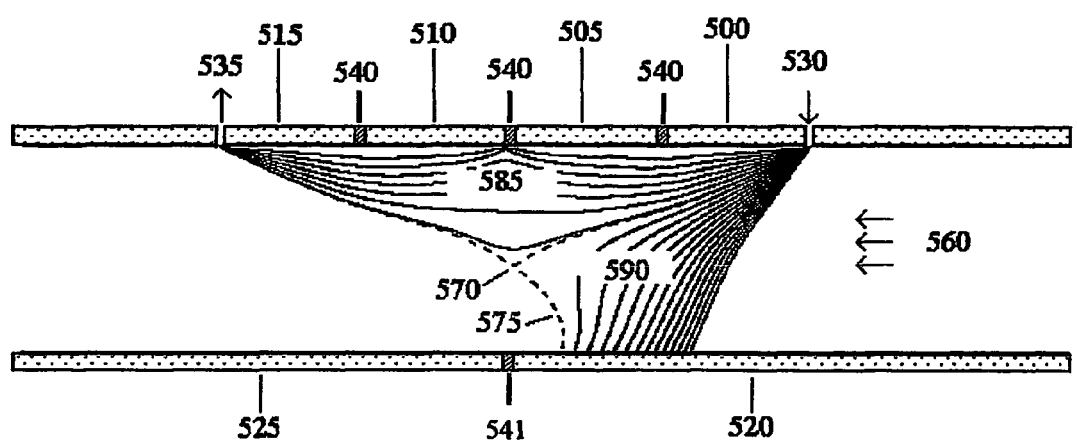

The range of mobilities of the ions that can reach the outlet is adjusted by varying the voltages on the top middle elements. FIG. 5a shows various ion trajectories when $V_{mr}$*=−0.28 ($V_{ml}$*=0.28). There is a stagnation trajectory, shown as a dashed curve, that passes through an ion stagnation point (570). The ion stagnation trajectory is a single curve from the inlet (530) to the stagnation point (570), where it splits into two branches, one branch (575B) goes to the top middle right element (505), the other branch (575B) goes to the bottom left element (520). As was also seen in FIG. 2, this splitting into branches beyond the stagnation point is a common feature of stagnation trajectories. The ion stagnation point (570) corresponds to a K of 1.622 (=$K_s$). There is a set of trajectories (580) for ions with K<$K_s$ These ions are focused on the top right middle element (505). There is another set of ion trajectories (590) for ions with K>$K_s$ that hit the bottom right element (520). For this particular combination of voltages, the ion filter is closed, with no ions reaching the indicated outlet (535).

As $V_{mr}$* is increased slightly to −0.27 ($V_{ml}$*=0.27) (FIG. 5b), two stagnation points (571,570) appear for K of 1.594 ($K_{s1}$, 571) and 1.601 ($K_{s2}$, 570). The ion trajectories for ions with K<$K_{s1}$ (580) strike the top middle rigid element (505) while the ion trajectories for ions with K>$K_{s2}$ (590) strike the bottom right element (520). Ions such that $K_{s1}$<K<$K_{s2}$ can pass through the filter and are focused on the outlet. The trajectories of these ions are marked as 585 in the drawing. As in the three element device, the focusing arises from the symmetry of the device and the fact that the ion streamfunction is a constant. The Δ/K for such a device is 0.0043, where ΔK=$K_{s2}$-$K_{s1}$, raising the possibility of a resolution as high as 228. Provided diffusion and/or space charge do not significantly reduce the resolution, such a low-pass filter could be used for high resolution mobility analysis and would act like a DMA.

Increasing $V_{mr}$* to −0.2 ($V_{ml}$*=0.2) (FIG. 5c), allows ions with 1.133<K<1.485 to pass to the outlet. In this case ΔK/K of 0.249 which equates to a resolution of only 4. A device with such low resolution however, could not be used for mobility analysis but could be used as a filter for another tandem downstream device. For example, the downstream device may be sensitive to space charge. Pre-filtering so as to remove any undesirable high and low mobility ions may reduce space charge and improve the performance of the downstream device.

Increasing $V_{mr}$* to above −0.15 ($V_{ml}$*=0.15) (FIG. 5d) allows virtually all ions with K<1.422 to pass through to the outlet and acts like a low-pass filter or CMA. Indeed, when $V_{mr}$=0, which means there is no voltage difference between adjacent top elements, the six element device would behave like a three element device. It should be mentioned that all the specific numbers for the voltages and the associated K values are for illustrative purposes only. Other configurations and therefore other values of these parameters can be used. For example, the top middle elements (505,510) can be either longer or narrower, the inlet and outlet may be closer or farther apart. Such changes in configurations should be obvious to anyone skilled in the art. The behavior of a device could be determined by solving the appropriate equations (i.e. Laplace's Equation for the electric field and either Laplace's equation or the Navier-Stokes equation for the flow field) for the specific element lengths and locations and then mapping the ion trajectories as described above. It is also possible to locate the ion outlet at different positions than the one indicated. For example, an ion outlet position on the bottom right (520) element would act like a DMA outlet because the high mobility ions strike that element according to mobility. An element located at the focal point of the ions on the top middle right element (505), on the other hand, will act as a CMA outlet.

Use of Auxiliary Flows

Figure 6A:
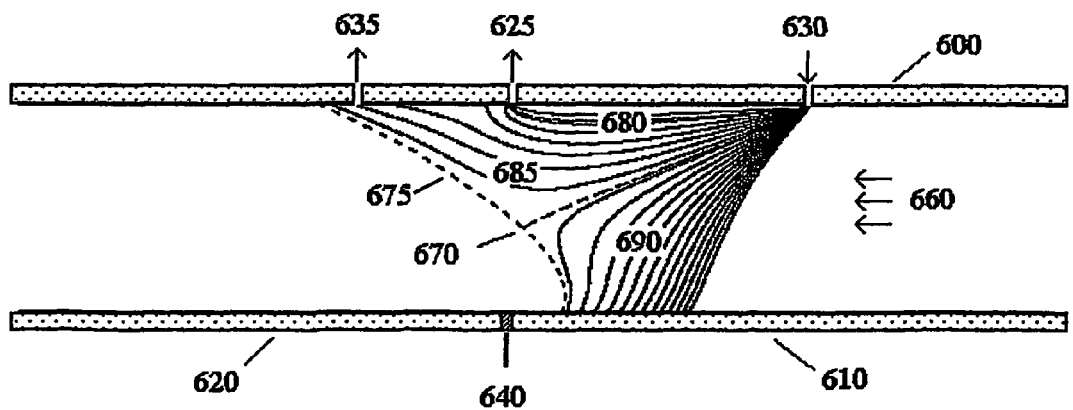
FIG. 6a shows a schematic cross-sectional view of a three element device with an auxiliary outlet flow.

We have noted the control advantages offered by MAs with junction and stagnation points. On the other hand, the focusing feature observed may be a disadvantage in specific applications, such as when a traditional DMA response is desired in combination with the isopotential feature introduced here. We have noted that focusing is forced by the fact that the fluid streamfunction takes the same value at the inlet and outlet points. The CMA could then be turned into a DMA by forcing the streamfunction Ψ to take different values $Ψ_1$ and $Ψ_2$ at the injection and sampling points, respectively. Physically this can be achieved by introducing and/or extracting a net flow of substantially ion-free sheath gas somewhere between the injection and sampling points. This net flow of sheath gas which changes the streamfunction between the ion inlet and outlet is referred to as auxiliary flow. If auxiliary flow is introduced in a configuration akin to that of FIG. 2, some ion trajectories would return to the collector wall held at the same potential as the injection port. The critical condition for this to happen is that K=($Ψ_1$-$Ψ_2$)/($Λ_1$-$Λ_2$). Since now $Ψ_1$ and $Ψ_2$ differ from each other, $Λ_1$-$Λ_2$ must also be different and only a unique mobility K will reach the sampling point, held at a fixed electrical streamfunction Λ. FIG. 6a schematically shows a device similar to that in FIG. 2 but with one auxiliary flow outlet (625) located directly above the junction (640) in the bottom plate. In this device sheath gas (660) flows as indicated from right to left between two parallel plates. As in FIG. 2, the bottom plate has two elements—a bottom left (620) and a bottom right (610) element separated by a junction (640). The ion inlet (630) is on the top plate (600) upstream form the junction (640). Low mobility ions are entrained by and extracted through the auxiliary flow outlet (625). The set of trajectories for these ions is marked as 680. The set of trajectories for the high mobility ions (690) pass below the indicated stagnation trajectory (675) (dashed lines) and stagnation point (670) and strike the bottom right element (610). The trajectories for ions with mobilities in between the high and low (685) are not focused and strike the top plate (600) downstream of the auxiliary outlet (625) at points that depend on the ion mobility. Ions with higher mobilities will strike the plate farther down stream than the lower mobility ions. An outlet (635) located upstream from the stagnation trajectory but downstream of the auxiliary outlet would be a DMA outlet.

Figure 6B:
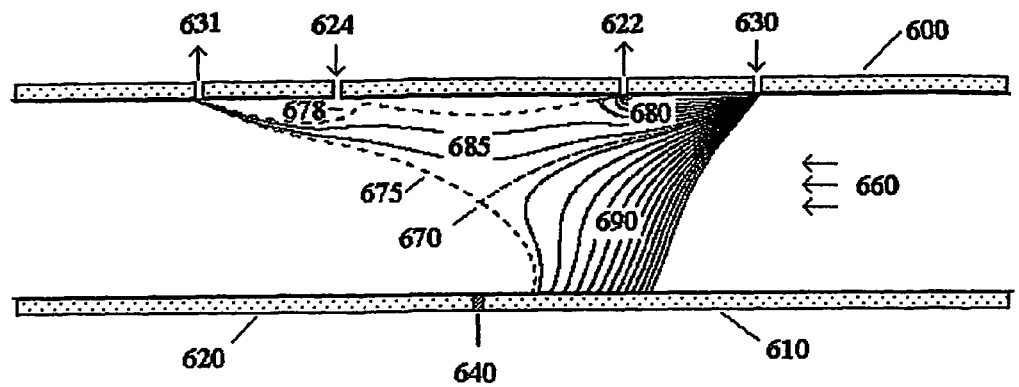
FIG. 6b shows a schematic cross-sectional view of a three element device with auxiliary outlet and auxiliary inlet flows.

More than one auxiliary flow can be introduced. As shown in FIG. 6b for a particular instance in which the net auxiliary flow in and out cancel each other exactly. In this figure, the top middle right element (505) of FIG. 5 is replaced by an orifice or slit through which auxiliary fluid is extracted (622) and the middle top left element (510) is replaced with an orifice or slit in which auxiliary fluid is input (624). Note that the figure is schematic, as the auxiliary flow introduced in 624 should preferably enter in a sufficiently smooth and streamlined fashion such that the flow field remains laminar. This device has three elements: the top plate (600) and a bottom left (620) and bottom right (610) elements separated by a junction (640). This input/extraction of auxiliary fluid has a similar effect on the ion trajectories as the middle elements (505,510) in FIG. 5. As in FIG. 5, the device shown in FIG. 6b has two stagnation points: one near the auxiliary outlet (not marked) and the one marked 670. Low mobility ions (680) are extracted through the auxiliary outlet (622) while the high mobility ions (690) strike the bottom right element (610). The ions between these extremes of mobilities (685) are focused on the indicated outlet (631). The collected mobility range ("bandwidth") of this device can be manipulated by varying the auxiliary flow rate. In order to maintain focusing, and decrease in the auxiliary flow outlet must be matched by a decrease in the auxiliary flow inlet so the net auxiliary flow is zero. Decreasing the auxiliary flow rate will widen the bandwidth, while increasing the auxiliary flow will narrow the bandwidth, much in the same way that changing the top middle element voltages in FIG. 5 changed the bandwidth. This means that auxiliary flows into/out of the analyzing region may be used as an alternative to additional elements to produce the desired ion separation.

It should be mentioned that an auxiliary flow outlet (suction) may also serve as an ion collector outlet. Indeed the auxiliary flow outlets in FIGS. 6a and b also serve as CMA ion collector outlets. One can easily imagine a device which has several auxiliary flow outlets which serve the dual functions of changing the stream function and as outlets for sampling ions. A device with multiple ion collector outlets is another unique feature of this invention. It should be mentioned that while, al auxiliary into the analyzing region flow should be substantially ion-free, auxiliary flow out of the analyzing region may contain extracted ions.

A Two Element Device

Figure 7A:
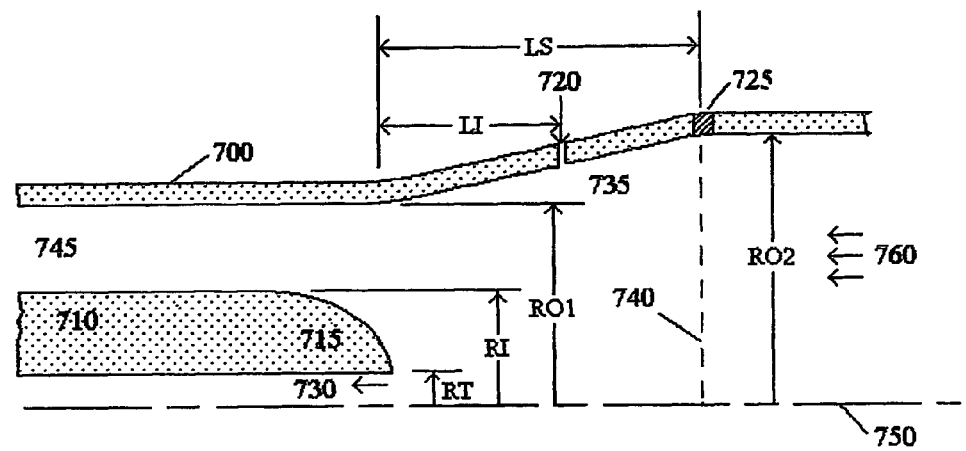
FIG. 7a shows a schematic cross-sectional view of a two element device.

An interesting configuration of elements is shown in FIG. 7a. The device is axi-symmetric with three major structural components: an inner section (710), an outer section (700)

and an electrified screen (740). Note that screen 740 is of the non-perturbing type, as it is located substantially upstream of the analyzing region and has a flow cross section larger than that in the analyzing region. The modest contraction ratio between the screen and the analyzing region shown in the figure is just for purposes of illustrations, and considerably larger area rations may often be desirable. Another novel features of this device is that the inner section (710) and the outer section (700) can be carved from a single piece of conducting material. Carving from one piece allows for very accurate machining, and therefore, excellent alignment of the sections. Since the inner and outer sections are not electrically isolated from one another, they comprise a single element.

The inner section is cylindrical with radius RI on one end and is "bullet shaped" (715) on the other. The ion outlet (730) is a hole drilled through the center line (axis, 750) of the inner section (710). In operating this device, a fraction of the sheath gas is extracted through the outlet (730). The outer section is cylindrical with a radius RO1, blending into a larger cylinder of radius RO2. The conical blending section is referred to as the "trumpet (735)". The angle of the trumpet in this device is 17 degrees but other angles are possible. A metallic screen (740) is located a distance LS upstream from the tip of the bullet. It is electrified but insulated from the inner and outer sections and is, therefore, the second element of this two element device. A junction (725), therefore, exists between the electrified screen (740) and the outer section (700). Sheath gas (760) is introduced into the analyzing region through the screen (740) from right to left. The Sheath gas is accelerated as it passes through the converging trumpet. Most of the sheath fluid passes over the bullet (715) and through the annulus (745) between the inner (710) and outer sections (700) and discharges through holes drilled (not shown) between theses sections far downstream from the bullet. A fraction of the sheath fluid, however, is sucked through the outlet (730). Ions to be analyzed are introduced through an inlet slit (720) in the trumpet region (735) of the outer section a distance LI upstream from the outlet (730). An attractive potential difference is maintained between the screen (740) and the inner/outer sections. It is common practice in prior DMA devices to place a screen far upstream from the analyzing region in order to laminarize the sheath gas flow, which is the only purpose of the screen in such devices. In this device, the screen is electrified and serves to generate the electrical field in the analyzing region in addition to laminarizing the sheath gas flow. This screen differs also from Tammet's, in that Tammet's screens make the flow turbulent while the present screens make it laminar.

Figure 7B:
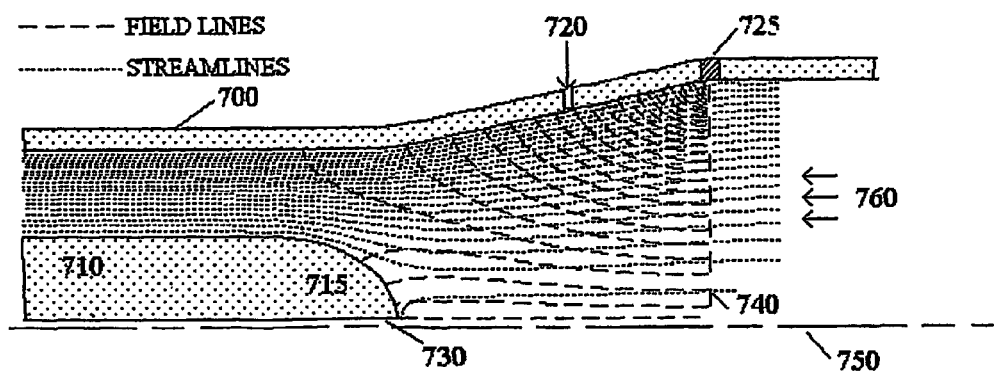
FIG. 7b shows the fieldlines and flow field in a two element device
Figure 7C:
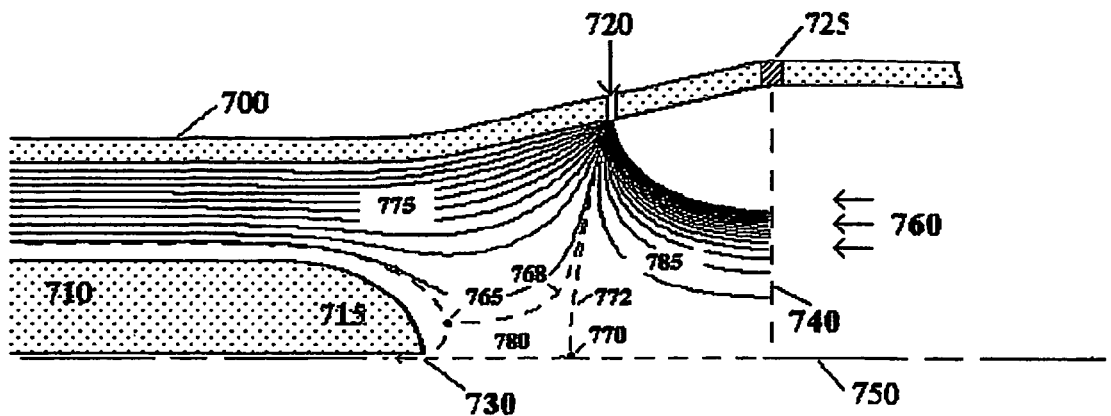
FIG. 7c-e show the trajectories in a two element device.

FIG. 7b shows the fieldlines (dashed lines) and streamlines (dotted lines) for this device for the indicated dimensions using RI as the characteristic length. In terms of dimensionless dimensions, for this device, RI=1, RT=0.05, RO1=2, RO2=2.764, LI=1.36 and LS=2.5 As drawn, the streamlines begin to the right of the electrified screen and are directed from right to left in the indicated direction of the sheath gas (760). The fieldlines, on the other hand, are directed from inner/outer element towards the screen. Near the inlet (720), the radial components of both E*(x*) and u(x*) point towards the axis. The axial components, on the other hand, oppose each other with the electric field tending to push the ions upstream, towards the screen and the sheath (760) tends to push them downstream towards the inner/outer annulus. One striking feature of this device is the vicinity of the bullet, E*(x) points away from the outlet. In all conventional DMA's (and in the above mentioned devices), E*(x) is always directed towards the outlet helping to collect the ions. In this device, E*(x) impedes the ion collection. The effects of u(x*) and E*(x*) on ion trajectories (solid curves) are shown in FIG. 7c for a device with a 1% inlet flow and 2% outlet flow.

The dashed curves indicate there are two ion stagnation trajectories (768,772) passing through ion stagnation points (765) and (770). One stagnation trajectory (768), corresponding to $K_{s1}$ passes through the off-axis stagnation point (765), where it branches. One branch goes around the bullet and into the inner/outer annulus while the other branch goes to the outlet (730). The other stagnation trajectory (772), corresponding to $K_{s2}$ passes through the on axis ion stagnation point (770) where it branches. One branch goes along the axis (750) to the screen while the other branch goes along the axis to the outlet (730). FIG. 7C shows two sets of ion trajectories. One set (775) is for ions with $K<K_{s1}$. These ions cannot reach the outlet (730) and are pushed downstream by the sheath gas through the inner/outer annulus and exit through a series of holes drilled into the back of the device (not shown). The other set of trajectories (785) is for ions with $K>K_{s2}$. These ions cannot reach the outlet and are attracted upstream to the screen (740). Only ions with a $K_{s1}<K<K_{s2}$ approach sufficiently close to the outlet (730) to be entrained by the fractional outlet flow and collected. One consideration in designing an MA is to separate the trajectories of the collected ion by the greatest distance from the other trajectories. If spatial separation were the only consideration, the fact that there is a deficiency of trajectories near the bullet indicates the strong possible resolving power of the device.

Figure 7D:
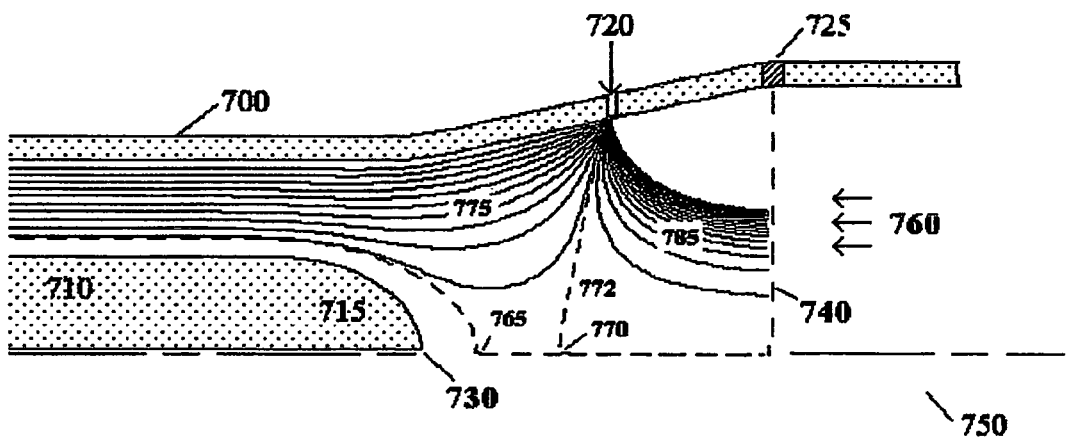
Figure 7E:
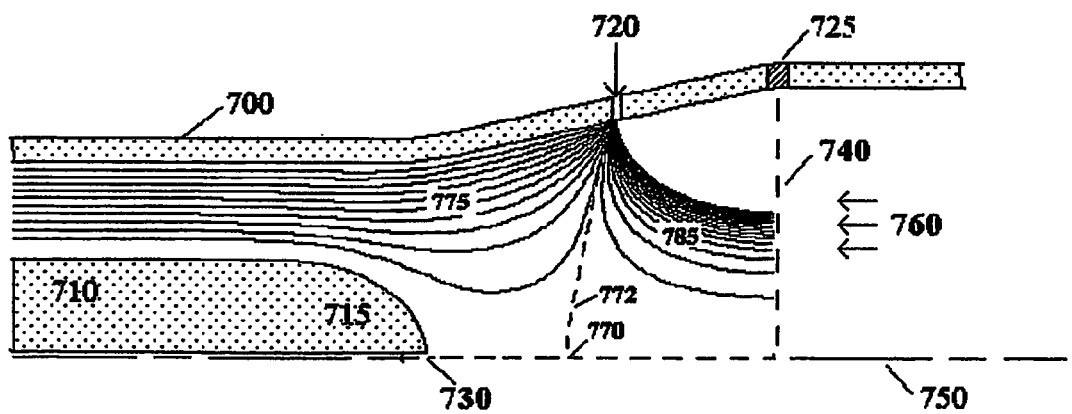

An essential feature of the above device clearly is the outlet flow percentage ($Q_o$). There is a threshold value for this outlet flow ($Q_{ot}$), below which there is no signal because the repulsive electrical field at the tip of the bullet impedes ion collection. This is shown in FIG. 7d for the case of $Q_o$=0.25%. In this figure, the two ion stagnation points (765,770) are on the axis and correspond to the same ion stagnation trajectory (772) but there is not enough outlet flow to counteract the outwardly directed electrical field. After passing ion stagnation point 765, the ions move tangentially around the bullet into the inner/outer annulus creating an ion-free region near the outlet (except by diffusion or space charge effects). It should be noted that the stagnation trajectory has a second branch that is not shown. This second branch in this cross-sectional view passes below the axis and around the underside of the bullet. Increasing the outlet flow ($Q_o$=0.5% FIG. 7e) allows ions within a very narrow range of K to reach the outlet (730). Hence, $Q_{ot}$ for this device is around 0.5%

Figure 8A:
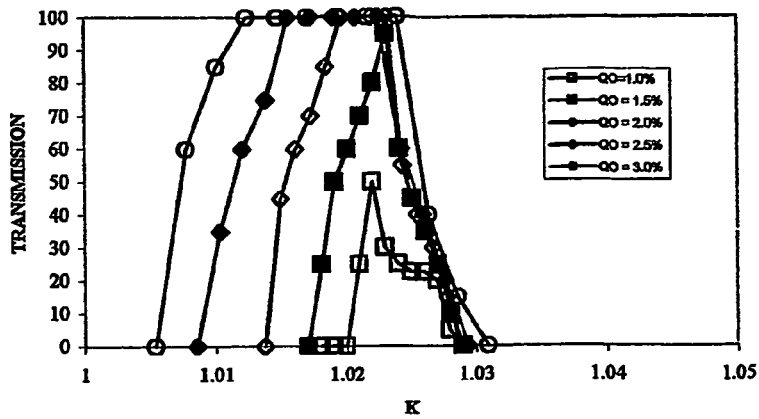
FIG. 8a-b Shows transmission as a function of K for various $Q_o$ values in a two element device a) $Q_i$=0 b) $Q_i$=1%

The effect of $Q_o$ on resolution and transmission is shown in FIG. 8a. In this figure, the transmission curves for various Qo when the inlet flow ($Q_i$) is much less than 1%. Notice that the transmission increases with increasing $Q_o$. For $Q_o$=1%, the transmission is 50% and increases to 95% as $Q_o$ is 1.5%. Full transmission is attained for $Q_o$>1.5%. While the transmission is low, at $Q_o$=1%, the resolution, as defined by Eqn. (3) is excellent (Res=205). Increasing $Q_o$ to 1.5%, increases the transmission but reduces the resolution to 170. The resolution decreases to 109, 73 and 55 for Qo=2%, 2.5% and 3%, respectively. So, there is a trade-off between transmission and resolution. Very high resolutions can be achieved but at the cost of low transmission. Increasing the inlet flow ($Q_i$) effects the transmission curves because a higher $Q_i$ means a higher ion velocity and more spread in the ions as they emerge from the inlet.

Figure 8B:
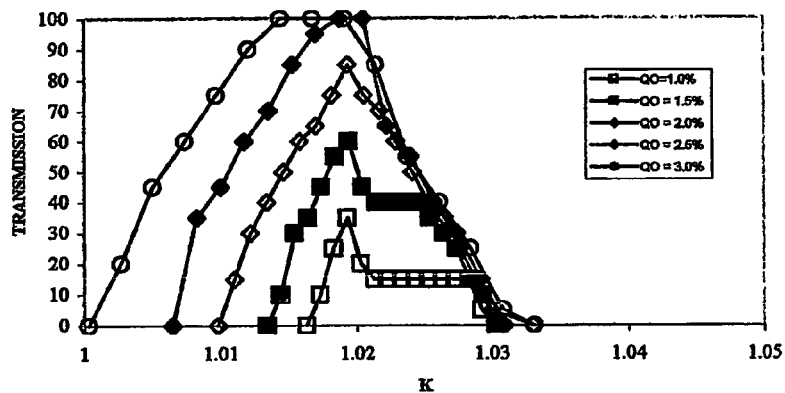
Figure 9:
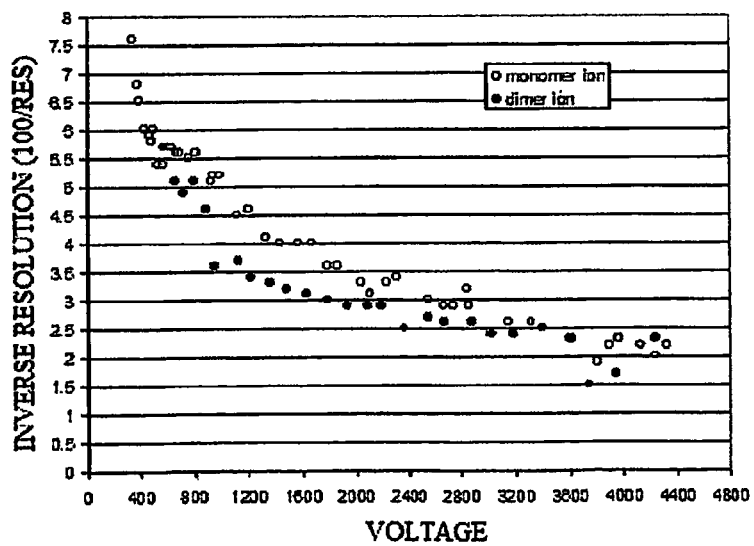
FIG. 9 shows the Inverse Resolution as a function of actual Voltage for a working two element device, where one of the elements is a screen located sufficiently upstream of the analyzing section, and provided with a flow cross section substantially larger than the flow cross section in the analyzing region so that the screen is non-perturbing.

FIG. 8b shows the transmission on curves for $Q_i$=1% with various $Q_o$. For $Q_o$=1%, the transmission is only 35%, but the resolution is 255 using the strict definition of resolution as the width at half height. At $Q_o$=1.5% the transmission increases to 60% and the resolution decreases to 93. That a high resolution MA can be built based on the principles presented here is shown in FIG. 9. This figure shows inverse resolution (IRes) as a function of Voltage for the mobility analysis of teraheptylammonium+monomer ion ($Z=0.96$ cm$^2$/V/s) and dimer ion ($Z=0.67$ cm$^2$/V/s) for a working two element device. In the working device, the actual dimensions are RI=0.75", RO1=1.5", RO2=2.073", LS=1.875", LI=1.02" and RT=0.05". The ion outlet (730) was positioned at the throat of the trumpet where the trumpet transitions to a cylinder). The inlet and outlet flow rates were maintained at 1% and 2% of the total sheath gas flow rate, respectively. Note that the inverse resolution can be as low as 2% [and with some data points as low as 1.9% for the monomer ion and as low as 1.5% for the dimer ion]. (Martinez-Lozano, Labowsky, Fernandez de la Mora, 2004, in preparation). Similar to the other devices shown above, this device is also isopotential. The inlet (720) and outlet (730) are on the same element. The two element device, however, needs an outlet flow in order to collect the ions. Further, the sheath gas flow is accelerating in the analyzing region and the outlet is on the axis of the device.

According to one aspect of the current invention, the sheath gas is accelerated immediately downstream of the screen and this acceleration coupled with the proper screen wire size and transparency (de La Mora, Diffusion Broadening in Converging Mobility Analyzers, J. Aerosol Science, Vol. 33, pp. 411-437, 2002) helps laminarize the flow allowing for high Reynolds number flow in the analyzing region. A Reynolds number in excess of 30,000 was achieved in the working two element device mentioned above. Hence, in contrast with Tammet's designs, the presence of the electrified screen in this device does not prevent keeping the flow laminar at rather high Reynolds numbers.

Another possible novel feature of this device, is to use the screen (740) as a "high pass" CMA outlet for all the ions with $K>K_{s2}$. This is possible because the screen (740) is insulated by the junction (725). Since the screen (outlet) is upstream from the inlet, the outlet (screen) is upstream from the inlet and is a non-isopotential. There are several possible variations of the screen as collector idea. The screen could be made to act like a DMA by introducing a junction and a second element on the outer section upstream from the inlet and downstream of the screen. Such a device would then have three elements and two junctions. By maintaining an attractive voltage on the upstream outer section element, the highest K ions would be attracted to this new upstream outer element. Some ions with somewhat lower K values, however will still strike the screen. Hence by using this configuration, the screen-collector would act like a DMA outlet (collector).

There are many other possible devices that can be made based on the disclosed principles. The two element configuration could be made into a three-element device by insulating the inner section from the outer section, making the inner section another element. A bias voltage on the inner section (now element) may have certain desirable characteristics for collecting ions. Such a device with an attractive bias voltage on the inner section would decrease the amount of outlet flow required to collect ions. Conversely, a slightly repulsive bullet bias voltage may improve the resolution. While this device with a bias voltage would not be isopotential, it may be considered to be "nearly isopotential." A nearly isopotential device may be considered one in which the absolute value of the voltage difference between the inlet and outlet is less than 60% of the absolute value of the maximum voltage difference between the inlet and any other element in the device. In this two element device, this maximum voltage difference is the voltage difference between the inlet and the screen.

Axial Ion Inlet Devices

Figure 10:
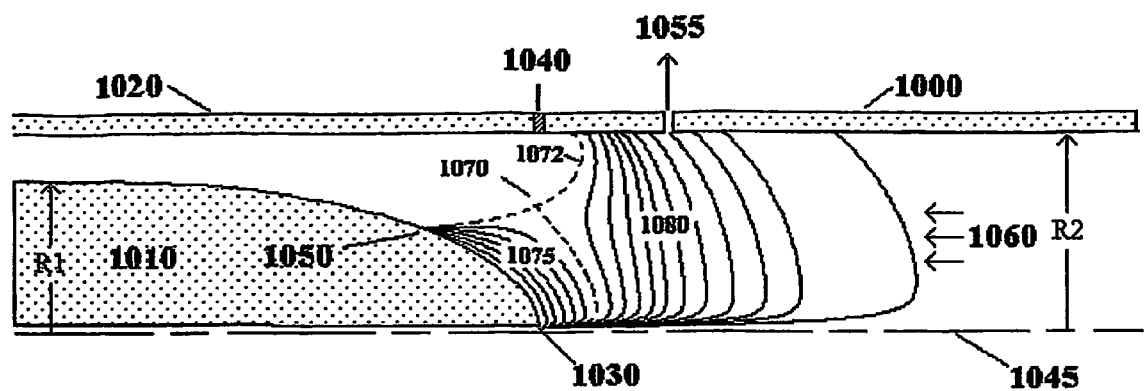
FIG. 10 shows a schematic cross-sectional view and ion trajectories in an axial ion inlet device.

The principles demonstrated in the above examples can be used to create many other devices. In the two element device, the ions were injected on the outer section and collected on the axis. It is also possible to have the ion inlet on the axis. FIG. 10 shows the ion trajectories in one such axi-symmetrical device. This device consists of an outer cylinder (1000, 1020) of radius $R_2$ inside of which is an inner element (1010). This inner element (1010) is cylindrical ($R_1$) on one end bullet shaped on the other. The characteristic length for this device is $R_1$. For this particular device shown, $R_2=1.3 R_1$. The outer cylinder has two elements separated by a junction (1040). The outer right element (1000) voltage is $V_{or}$ the outer left element (1020) voltage is $V_{ol}$ and the bullet (inner element (1010)) voltage is $V_b$.

The bullet in this example is ellipsoidal in shape with an axis ratio of 3:1, but other values are possible. Choosing the characteristic voltage difference as the voltage difference between the outer left and right elements, the dimensionless voltages are $V^*_{ol}=0.5$, $V^*_b=0$ and $V^*_{or}=-0.5$ in this example. Hence the outer right element (1000) is attractive and the outer left element (1020) is repulsive with respect to the ion inlet (1030). As indicated, sheath gas (1060) flows from right to left.

The behavior of this device is quite interesting. The dashed-trajectory (1072) is the stagnation trajectory which branches out after passes through the indicated stagnation point (1070). Ions that pass through this point have a K of $K_s$. Upon leaving the inlet, the electrical fields are such that the ions are attracted upstream by the outer right element (1000). Opposing this upstream motion is the downstream action of the sheath gas (1060). Ions with $K<K_s$ have a mobility that is too low to penetrate far upstream and are pushed downstream by the sheath gas. If the outer right element (1020) were not repulsive, these ions would pass through the annular region between the inner and outer elements. However, the outer right element is repulsive, and of sufficient strength to force these ions back to the inner element (1010). The trajectories for ions with $K<K_s$ are marked 1075. If an outlet were placed at the strike point (1050) on the inner element, such an outlet would be an isopotential CMA Outlet. Further such an outlet is on the same element as the inlet and the ions are focused on this outlet.

Ions with $K>K_s$ can penetrate further upstream after leaving the inlet but eventually reach a point where the downstream action of the sheath gas is greater than the upstream (axial) attraction of the outer right element (1000). The electrical field in this region, however, has a radial as well as an axial component. While the axial component is not sufficiently strong to pull the ions upstream against the sheath gas, the radial component attracts the ions to the outer right element (1000). The ions strike this element at points which are dependent on the ion mobility. Hence, if an outlet (1055) were located on this element, it would be a DMA outlet. Such an outlet, however, would not be isopotential, but the dimensionless voltage difference between the inlet ($V^*_b$) and the outlet ($V^*_b-V^*_{or}=0.5$) is half that of the Prior Art DMA shown in FIG. 1 and half the maxi voltage difference that exists in the device. This maximum dimensionless voltage difference would be the voltage difference between the outer left and outer right voltages ($V^*_{ol}-V^*_{or}=1$, since $V_{ol}-V_{or}=V_c$). Also note that as shown, the DMA outlet (1055) is upstream from the inlet (1030).

This device shows many of the same properties of the other devices discussed in this patent: 1) the presence of a junction 2) the presence of an ion stagnation point 3) an isopotential outlet 4) an outlet that is on the same element as the inlet 5) an outlet that is at the focal point of the ions. In addition, however, this device 6) shows an inlet that is on the axis of the device and 7) an outlet that is upstream from the inlet.

Figure 11:
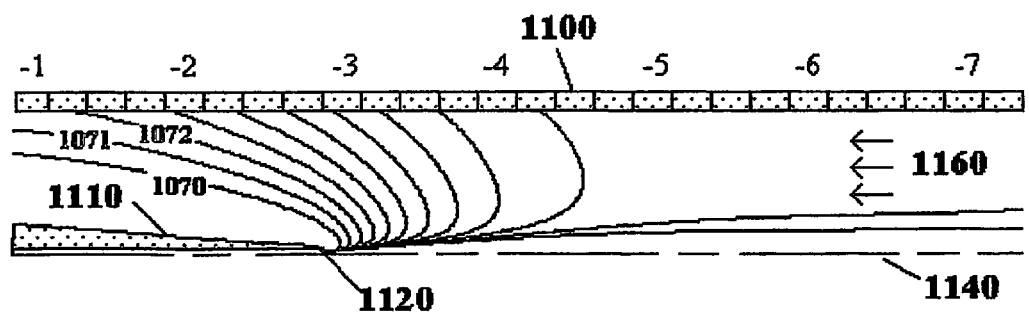
FIG. 11 shows a schematic cross-sectional view and ion trajectories in an axial ion inlet device with multiple junctions on the outer cylinder.

There are many variations on this device. As shown, the junction (1040) is located radially above the ion inlet (1030). The inlet could be upstream or downstream of the junction. The dimensionless voltages of the elements can also be varied. The bullet can have a different shape than the one shown provided that the shape does not introduce any flow irregularities in the analyzing region. All such changes would affect the value of $K_s$ and the location of the ion focal point. One could easily envision a device with more than two outer elements (more than one junction). Indeed, it would be possible to have several outer elements with voltages such that the resulting electrical field has a linear axial component. One such device is shown in FIG. 11

This device consists of an outer cylinder (1100) and an inner cone shaped bullet. The outer cylinder contains many junctions, indicated by perpendicular lines inside the outer cylinder (1100). The numerous elements in the outer cylinder are between the junctions. The dimensionless voltages on each element are set such that there is a linear progression in the voltages from down stream to upstream. The negative numbers above the outer cylinder (1100) show the approximate value of the dimensionless voltage on the elements below the numbers. This progression is such that the upstream voltage is lower (more attractive) than the downstream voltages. The bullet in this case has a large axis ratio and approximates a cone, but can have other shapes. The ion inlet (1120) is a small hole at the tip of the bullet which is at ground. The trajectories of the ions are with various K values in intervals of ΔK of 0.1 are shown. The trajectory that is farthest to the left (1070) is for K=0.2. The next trajectory (1071) is for K=0.3 and so forth. The sheath gas (1160) flows into the device from right to left. An outlet could be placed anywhere on an element in the outer cylinder (no outlet is indicated in the drawing). The presence of stagnation points is not obvious from this drawing, but they do exist in the vicinity of the junctions. Indeed, this device has many ion stagnation points. This device is not isopotential but the large spatial separation in the trajectories is an indication that in the absence of diffusion and space charge effects, the resolution of such a device may be high. It should also be noted that while the outer cylinder has a linear voltage distribution, but other voltages distributions are possible.

In the all the above axi-symmetrical (AS) devices, it may be desirable to make the outer element(s) conical rather than cylindrical so the sheath gas is accelerating in this region to reduce the possibility of sheath gas flow irregularities. For the 2D devices, the plates may be slightly converging to accelerate the flow. It should also be remembered that 2D equivalents of the AS devices can be made and visa versa.

This patent specification shows only a few of the many possible embodiments of the invention. Many other devices can be made based on the principles disclosed here. In the manner described above, the present invention thus provides a method and apparatus to separate ions based on their ion mobilities. While this invention has been described with reference to the certain embodiments, these embodiments are illustrative only and not limiting, having been presented by way of example. Other modifications will become apparent to those skilled in the art by study of the specification and drawings. It is thus intended that the following appended claims include such modifications as fall within the spirit and scope of the present invention.

What we claim is:
1. A method for separating ions in a mobility analyzer having an inlet and an outlet said method comprising the following steps:
    a. introducing a stream of ions into an analyzing region through said inlet;
    b. introducing laminar sheath gas flow into said mobility analyzer upstream from said analyzing region;
    c. maintaining of said laminar sheath gas flow as substantially laminar in the said analyzing region;
    d. providing an electrical field in said analyzing region wherein said electrical field is generated by elements separated by junctions;
    e. using the said laminar sheath gas flow and the said electrical field to separate the ions by mobility in the said analyzing region;
    f. collecting said separated ions within a range of electrical mobilities through said outlet.
2. A method according to 1, wherein the said inlet and said outlet are on the same element.
3. A method according to 1, wherein the voltage difference between said inlet and said outlet is zero.
4. A method according to 1, wherein the voltage difference between said inlet and said outlet is less than the maximum voltage difference between the inlet and any other element.
5. A method according to 1, wherein an ion stagnation point exist in the analyzing region.
6. A method according to 1, wherein ions are focused on said outlet.
7. A method according to 1, wherein said analyzing region is in a region where said laminar sheath gas flow is accelerating.
8. A method according to 1, wherein an electrified screen is used to provide the electric field in the analyzing region.
9. A method according to 1, wherein a conducting screen is used to collect ions.
10. A method according to 1, wherein ions are collected on the axis of the device.
11. A method according to 1, wherein the outlet for the ions is on an element which has a voltage which is repulsive to the ions.
12. A method according to 1, wherein the inlet for the ions is on the axis of the device.
13. A method for separating ions in a mobility analyzer having an inlet and an outlet said method comprising the following steps:
    a. introducing a stream of ions into an analyzing region through said inlet;
    b. introducing laminar sheath gas flow into said mobility analyzer upstream from said analyzing region;
    c. maintaining of said laminar sheath gas flow as substantially laminar in the said analyzing region;
    d. providing an electrical field in said analyzing region wherein said electrical field is generated by elements charged to various voltages;
    e. providing auxiliary sheath gas flows;
    f. using the said laminar sheath gas flow said electrical field and said auxiliary sheath gas flows to separate the ions by mobility in the said analyzing region;
    g. collecting the separated ions in said outlet.
14. A method according to 13, wherein the said inlet and said outlet are on the same element.
15. A method according to 13, wherein the voltage difference between said inlet and said outlet is zero.
16. A method according to 13, wherein the voltage difference between said inlet and said outlet is less than the maximum voltage difference between any two said elements.

17. A method according to 13, wherein ion stagnation points exist in the analyzing region.

18. A method according to 13, wherein ions are focused on said outlet.

19. A method according to 13 wherein the laminar sheath gas flow is accelerating in the analyzing region.

20. A method according to 13, wherein a conducting screen is used to collect ions.

21. A method according to 13, wherein ions are collected on the axis of the device.

22. A method according to 13, wherein the outlet for the ions is on an element which has a voltage which is repulsive to the ions.

23. A method according to 13 wherein the inlet for the ions is on the axis of the device.

24. A method according to 13 wherein said elements are separated by junctions.

25. A method for separating ions in a mobility analyzer having an inlet and an outlet said method comprising the following steps:
   a. introducing a stream of ions into said analyzing region through said inlet;
   b. introducing said laminar sheath gas flow into said mobility analyzer upstream from said analyzing region;
   c. maintaining of said laminar sheath gas flow as laminar in the said analyzing region;
   d. providing an electrical field in said analyzing region by charging elements to various voltages;
   e. the said laminar sheath gas flow and the said electrical field separate the ions by mobility in the said analyzing region;
   f. collecting said separated ions on said outlet, said outlet being on the axis of the said analyzing region.

26. A method according to 25 wherein said elements are separated by junctions.

27. A method according to 25 wherein the voltage difference between said inlet and said outlet is zero.

28. A method according to 25, wherein the voltage difference between said inlet and said outlet is less than the maximum voltage difference between any two said elements.

29. A method according to 25, wherein ions are focused on said outlet.

30. A method according to 25, wherein a conducting screen is used to collect ions.

31. A method according to 25, wherein the outlet for the ions is on an element which has a voltage which is repulsive to the ions.

32. A method according to 25 wherein the inlet for the ions is on the axis of the device.

33. A method according to 25 wherein said elements are separated by junctions.

34. A method for separating ions in a mobility analyzer having an inlet and an outlet said method comprising the following steps:
   a. introducing a stream of ions into said analyzing region through said inlet;
   b. introducing laminar sheath gas flow into said mobility analyzer upstream from said analyzing region;
   c. maintaining of said laminar sheath gas flow as laminar in the said analyzing region;
   d. providing an electrical field in said analyzing region by charging elements to various voltages;
   e. using said laminar sheath gas flow and the said electrical field to separate the ions by mobility in the said analyzing region;
   f. collecting said separated ions in said outlet, said outlet being upstream from said inlet.

35. A method for separating ions in a mobility analyzer having an inlet and an outlet said method comprising the following steps:
   a. introducing a stream of ions into an analyzing region through said inlet;
   b. introducing laminar sheath gas flow into said mobility analyzer upstream from said analyzing region;
   c. maintaining of said laminar sheath gas flow as substantially laminar in the said analyzing region said sheath gas flow having a Reynolds number in excess of 2000 in said analyzing region;
   d. providing an electrical field in said analyzing region wherein said electrical field is generated;
   e. using the said laminar sheath gas flow and the said electrical field to separate the ions by mobility in the said analyzing region;
   f. collecting the separated ions in an outlet wherein the voltage difference between said inlet and said outlet is zero.

36. A method for separating ions in a mobility analyzer having an inlet and an outlet said method comprising the following steps:
   a. introducing a stream of ions into an analyzing region through said inlet;
   b. introducing laminar sheath gas flow into said mobility analyzer upstream from said analyzing region;
   c. maintaining of said laminar sheath gas flow as substantially laminar in the said analyzing region;
   d. providing an electrical field in said analyzing region wherein said electrical field is generated;
   e. using the said laminar sheath gas flow and the said electrical field to separate the ions by mobility in the said analyzing region;
   f. collecting the separated ions in an outlet wherein the voltage difference between said inlet and said outlet is less than the maximum voltage difference between any two said elements.

37. A method for separating ions in a mobility analyzer having an inlet and an outlet said method comprising the following steps:
   a. introducing a stream of ions into an analyzing region through said inlet;
   b. introducing laminar sheath gas flow into said mobility analyzer upstream from said analyzing region;
   c. maintaining of said laminar sheath gas flow as substantially laminar in the said analyzing region;
   d. providing an electrical field in said analyzing region wherein said electrical field is generated;
   e. using the said laminar sheath gas flow and the said electrical field to separate the ions by mobility in the said analyzing region;
   f. collecting the separated ions in said outlet wherein the said inlet and said outlet are on the same element.

38. A method for separating ions in a mobility analyzer having an inlet and an outlet said method comprising the following steps:
   a. introducing a stream of ions into an analyzing region through said inlet;
   b. introducing laminar sheath gas flow into said mobility analyzer upstream from said analyzing region;
   c. maintaining of said laminar sheath gas flow as substantially laminar in the said analyzing region;
   d. providing an electrical field in said analyzing region wherein said electrical field is generated by elements charged to various voltages;

e. using the said laminar sheath gas flow and the said electrical field to separate the ions by mobility in the said analyzing region said analyzing region containing an ion stagnation point;
f. collecting the separated ions in an outlet wherein the voltage difference between said inlet and said outlet is less than the maximum voltage difference between said inlet and any one of said elements.

39. A method according to 25 wherein the laminar sheath gas flow is accelerating in the analyzing region.

* * * * *

UNITED STATES PATENT AND TRADEMARK OFFICE
CERTIFICATE OF CORRECTION

PATENT NO. : 7,626,161 B2
APPLICATION NO. : 10/556521
DATED : December 1, 2009
INVENTOR(S) : Labowsky et al.

It is certified that error appears in the above-identified patent and that said Letters Patent is hereby corrected as shown below:

Column 2, line 20, replace "or extracted bt electrical means" with --or extracted by electrical means--;

Column 3, line 6, replace "gas flow is idea, in the sense" with --gas flow is ideal, in the sense--;

Column 7, line 50, replace "used to obtained the desired" with --used to obtain the desired--;

Column 12, line 60, replace "while, al auxiliary into the analyzing region flow should be" with --while, all auxiliary flow into the analyzing region should be--.

Signed and Sealed this

Ninth Day of February, 2010

David J. Kappos
*Director of the United States Patent and Trademark Office*